(12) United States Patent
Weiner et al.

(10) Patent No.: US 9,670,120 B2
(45) Date of Patent: Jun. 6, 2017

(54) PROCESS FOR PRODUCING ETHANOL USING A SOLID CATALYST

(71) Applicant: Celanese International Corporation, Irving, TX (US)

(72) Inventors: Heiko Weiner, Pasadena, TX (US); Zhenhou Zhou, Houston, TX (US)

(73) Assignee: CELANESE INTERNATIONAL CORPORATION, Irving, TX (US)

( * ) Notice: Subject to any disclaimer, the term of this patent is extended or adjusted under 35 U.S.C. 154(b) by 100 days.

(21) Appl. No.: 14/606,808

(22) Filed: Jan. 27, 2015

(65) Prior Publication Data

US 2016/0214915 A1    Jul. 28, 2016

(51) Int. Cl.
*C07C 29/149* (2006.01)
*B01J 37/02* (2006.01)
(Continued)

(52) U.S. Cl.
CPC ......... *C07C 29/149* (2013.01); *B01J 23/6482* (2013.01); *B01J 23/6522* (2013.01); *B01J 23/89* (2013.01); *B01J 23/8933* (2013.01); *B01J 23/8966* (2013.01); *B01J 35/008* (2013.01); *B01J 37/0244* (2013.01); (Continued)

(58) Field of Classification Search
CPC .... B01J 23/6482; B01J 23/6522; B01J 23/89; B01J 23/8933; B01J 23/8966; B01J 35/008; B01J 37/0244; B01J 2523/00; B01J 35/0026; B01J 35/0066; B01J 35/023; B01J 35/026; B01J 35/1009; B01J 35/1014; B01J 35/1019; B01J 35/1023; B01J 35/1042; C07C 29/149
See application file for complete search history.

(56) References Cited

U.S. PATENT DOCUMENTS 4,199,438 A    4/1980 Antos
4,398,039 A    8/1983 Pesa et al.
(Continued)

FOREIGN PATENT DOCUMENTS

CN    102247856 A    11/2011
CN    102451722 A    5/2012
(Continued)

OTHER PUBLICATIONS

International Search Report and Written Opinion of the International Searching Authority mailed on Jun. 16, 2015 for PCT Patent Application No. PCT/US2015/013122, 12 pages.
(Continued)

*Primary Examiner* — Jafar Parsa
*Assistant Examiner* — Medhant Bahta
(74) *Attorney, Agent, or Firm* — Kilpatrick Townsend & Stockton LLP (57) ABSTRACT

The present invention relates to a solid catalyst for producing ethanol from acetic acid, ethyl acetate, or mixtures thereof comprising a core region comprising a Group IIA metal and a surface region surrounding the core region and comprising one or more main metals. The total loading of the main metals in the catalyst is greater than or equal to 1 wt. %. Also more than 85% of main metals are located in the surface region, based on the total loading of the main metals in the catalyst. The surface region may comprise two or more layers.

19 Claims, 4 Drawing Sheets

(51) Int. Cl.
  *B01J 23/648* (2006.01)
  *B01J 23/652* (2006.01)
  *B01J 23/89* (2006.01)
  *B01J 35/02* (2006.01)
  *B01J 35/10* (2006.01)
  *B01J 35/00* (2006.01)

(52) U.S. Cl.
  CPC ........ *B01J 35/0026* (2013.01); *B01J 35/0066* (2013.01); *B01J 35/023* (2013.01); *B01J 35/026* (2013.01); *B01J 35/1009* (2013.01); *B01J 35/1014* (2013.01); *B01J 35/1019* (2013.01); *B01J 35/1023* (2013.01); *B01J 35/1042* (2013.01); *B01J 35/1047* (2013.01); *B01J 35/1061* (2013.01); *B01J 2523/00* (2013.01)

(56) References Cited

U.S. PATENT DOCUMENTS

| | | |
|---|---|---|
| 4,517,391 A | 5/1985 | Schuster et al. |
| 4,777,303 A | 10/1988 | Kitson et al. |
| 4,804,791 A | 2/1989 | Kitson et al. |
| 4,835,131 A | 5/1989 | DeJong |
| 5,149,680 A | 9/1992 | Kitson et al. |
| 5,292,916 A | 3/1994 | Matsuzaki et al. |
| RE35,377 E | 11/1996 | Steinberg et al. |
| 5,821,111 A | 10/1998 | Grady et al. |
| 6,204,417 B1 | 3/2001 | Fischer et al. |
| 6,232,352 B1 | 5/2001 | Vidalin |
| 6,495,730 B1 | 12/2002 | Konishi et al. |
| 6,657,078 B2 | 12/2003 | Scates et al. |
| 6,685,754 B2 | 2/2004 | Kindig et al. |
| 7,375,049 B2 | 5/2008 | Hayes et al. |
| 7,608,744 B1 | 10/2009 | Johnston et al. |
| 7,863,489 B2 | 1/2011 | Johnston et al. |
| 8,211,821 B2 | 7/2012 | Weiner et al. |
| 8,211,823 B2 | 7/2012 | Liang et al. |
| 8,309,772 B2 | 11/2012 | Weiner et al. |
| 8,471,075 B2 | 6/2013 | Johnston et al. |
| 8,501,652 B2 | 8/2013 | Johnston et al. |
| 8,536,236 B2 | 9/2013 | Lok et al. |
| 8,536,382 B2 * | 9/2013 | Jevtic .................. B01J 23/6527 568/885 |
| 8,865,609 B2 | 10/2014 | Zhou et al. |
| 2003/0105373 A1 | 6/2003 | Rende et al. |
| 2007/0270514 A1* | 11/2007 | Lok .......................... B01J 21/04 518/715 |
| 2010/0029996 A1 | 2/2010 | Danjo et al. |
| 2010/0030001 A1 | 2/2010 | Chen et al. |
| 2010/0030002 A1 | 2/2010 | Johnston et al. |
| 2010/0121114 A1 | 5/2010 | Weiner et al. |
| 2011/0190117 A1 | 8/2011 | Weiner et al. |
| 2012/0165589 A1 | 6/2012 | Partington |
| 2012/0296111 A1 | 11/2012 | Konigsmann et al. |
| 2013/0178661 A1 | 7/2013 | Zhou et al. |
| 2013/0178663 A1 | 7/2013 | Zhou et al. |
| 2013/0245332 A1 | 9/2013 | Weiner et al. |
| 2013/0245337 A1* | 9/2013 | Weiner ................ B01J 37/0244 568/885 |
| 2014/0171290 A1 | 6/2014 | Lopez et al. |
| 2015/0209762 A1 | 7/2015 | Weiner et al. |

FOREIGN PATENT DOCUMENTS

| | | |
|---|---|---|
| CN | 103100391 A | 5/2013 |
| CN | 103113187 A | 5/2013 |
| CN | 104275194 A | 1/2015 |
| DE | 10 2013 225 764 A1 | 6/2014 |
| EP | 0 175 558 A1 | 3/1986 |
| EP | 0653242 A1 | 5/1995 |
| EP | 2 583 751 A1 | 4/2013 |
| WO | 03/040263 A2 | 5/2003 |
| WO | 2006/059148 A1 | 6/2006 |
| WO | 2010/146332 A1 | 12/2010 |
| WO | 2011/053367 A1 | 5/2011 |
| WO | 2011/094713 A1 | 8/2011 |
| WO | 2013/101756 A1 | 7/2013 |
| WO | 2013/103850 A1 | 7/2013 |

OTHER PUBLICATIONS

International Search Report and Written Opinion of the International Searching Authority mailed on Sep. 24, 2015 for International Application No. PCT/US2015/013137, 11 pages.

Non-Final Office Action mailed on May 4, 2015 for U.S. Appl. No. 14/164,656, 7 pages.

* cited by examiner

PROCESS FOR PRODUCING ETHANOL USING A SOLID CATALYST

FIELD OF THE INVENTION

The present invention relates generally to processes for hydrogenating acetic acid to form ethanol and to novel solid catalysts for use in such processes. The solid catalysts have a core region and a surface region that comprises one or more main metals, wherein at least 85% of the main metals based on the total loading of the main metals are located in the surface region.

BACKGROUND OF THE INVENTION

Ethanol for industrial use is conventionally produced from petrochemical feed stocks, such as oil, natural gas, or coal, from feed stock intermediates, such as syngas, or from starchy materials or cellulosic materials, such as corn or sugar cane. Conventional methods for producing ethanol from petrochemical feed stocks, as well as from cellulosic materials, include the acid-catalyzed hydration of ethylene, methanol homologation, direct alcohol synthesis, and Fischer-Tropsch synthesis. Instability in petrochemical feed stock prices contributes to fluctuations in the cost of conventionally produced ethanol, making the need for alternative sources of ethanol production all the greater when feed stock prices rise. Starchy materials, as well as cellulosic material, are converted to ethanol by fermentation. However, fermentation is typically used for consumer production of ethanol, which is suitable for fuels or human consumption. In addition, fermentation of starchy or cellulosic materials competes with food sources and places restraints on the amount of ethanol that can be produced for industrial use.

As an alternative to fermentation, ethanol may be produced by hydrogenating acetic acid and esters thereof. Ethanol production via the reduction of acetic acid generally uses a hydrogenation catalyst. The reduction of various carboxylic acids over metal oxides has been proposed by EP0175558 and U.S. Pat. No. 4,398,039. U.S. Pat. No. 7,608,744 describes a process for the selective production of ethanol by vapor phase reaction of acetic acid at a temperature of about 250° C. over a hydrogenating catalyst composition either cobalt and palladium supported on graphite or cobalt and platinum supported on silica. U.S. Pat. No. 7,863,489 describes a process for the selective production of ethanol by vapor phase reaction of acetic acid over a hydrogenating catalyst composition to form ethanol is disclosed and claimed. In an embodiment of this invention, reaction of acetic acid and hydrogen over a platinum and tin supported on silica, graphite, calcium silicate or silica-alumina in a vapor phase at a temperature of about 250° C. U.S. Pat. No. 6,495,730 describes a process for hydrogenating carboxylic acid using a catalyst comprising activated carbon to support active metal species comprising ruthenium and tin. U.S. Pat. No. 8,309,772 discloses a process for selective formation of ethanol from acetic acid and includes contacting a feed stream containing acetic acid and hydrogen at an elevated temperature with catalyst comprising platinum and tin on a high surface area silica promoted with calcium metasilicate. U.S. Pat. No. 8,471,075 also discloses a process for selective formation of ethanol from acetic acid by hydrogenating acetic acid in the presence of first metal, a silicaceous support, and at least one support modifier. U.S. Pat. No. 6,204,417 describes another process for preparing aliphatic alcohols by hydrogenating aliphatic carboxylic acids or anhydrides or esters thereof or lactones in the presence of a catalyst comprising platinum and rhenium. U.S. Pat. No. 5,149,680 describes catalytic hydrogenation of carboxylic acids and their anhydrides to alcohols and/or esters in the presence of a catalyst containing a Group VIII metal, such as palladium, a metal capable of alloying with the Group VIII metal, and at least one of the metals rhenium, tungsten or molybdenum. U.S. Pat. No. 4,777,303 describes the productions of alcohols by the hydrogenation of carboxylic acids in the presence of a catalyst that comprises a first component which is either molybdenum or tungsten and a second component which is a noble metal of Group VIII on a high surface area graphitized carbon. U.S. Pat. No. 4,804,791 describes another production process of alcohols by the hydrogenation of carboxylic acids in the presence of a catalyst comprising a noble metal of Group VIII and rhenium. U.S. Pat. No. 4,517,391 describes preparing ethanol by hydrogenating acetic acid under superatmospheric pressure and at elevated temperatures by a process wherein a predominantly cobalt-containing catalyst is used and acetic acid and hydrogen are passed through the reactor, at from 210 to 330° C., and under 10 to 350 bar, under conditions such that a liquid phase is not formed during the process.

Hydrogenation catalysts having solid structures with layers have also been disclosed. US Pub. No. 2012/0296111 discloses an eggshell catalyst comprising an active metal selected from the group consisting of ruthenium, rhodium, palladium, platinum and mixtures thereof, applied to a support material comprising silicon dioxide, wherein the pore volume of the support material is 0.6 to 1.0 ml/g, determined by Hg porosimetry, the BET surface area is 280 to 500 m$^2$/g, and at least 90% of the pores present have a diameter of 6 to 12 nm, to a process for preparing this eggshell catalyst, to a process for hydrogenating an organic compound which comprises at least one hydrogenatable group using the eggshell catalyst, and to the use of the eggshell catalyst for hydrogenating an organic compound. EP2583751 discloses heterogeneous catalysts useful for selective hydrogenation of unsaturated hydrocarbons, comprising palladium and optionally a promoter, supported on a substrate, having an uncoated BET surface area of ≤9 m2/g, the surface being coated with an ionic liquid. U.S. Pat. No. 8,211,823 discloses a selective hydrogenation catalyst, with alumina as carrier, and palladium as active component that distributed on the surface of the carrier in an egg-shell form, characterized in that: provided that the catalyst is weighed 100%, it comprises 0.2-0.5 wt % active component Pd, 2-8 wt % aids lanthanum and/or cerium, and 2-8 wt % alkaline earth metal. U.S. Pat. No. 7,375,049 discloses a catalyst suitable for the dehydrogenation and hydrogenation of hydrocarbons comprises at least one first metal and at least one second metal bound to a support material. The at least one first metal comprises at least one transition metal, suitably a platinum group metal. The support material is provided with an overlayer such that acidic sites on the support material are substantially blocked. U.S. Pat. No. 4,835,131 discloses a catalyst, which may have an egg-shell or an egg-yolk type distribution for the catalytically active component, and may be used in diffusion limited processes as well as in processes wherein the feedstock may contain catalyst poisons, e.g. in residue conversion.

Processes for producing the eggshell catalysts are described in U.S. Pat. No. 8,536,236, CN103100391, CN102451722, and CN102247856.

Thus, further improvements to hydrogenation catalysts to increase conversion of acetic acid and selectivity to ethanol are needed to improve production of ethanol from acetic acid.

SUMMARY OF THE INVENTION

In a first embodiment, the invention is related to a solid catalyst for producing ethanol from acetic acid, ethyl acetate, or mixtures thereof comprising a core region, and a surface region surrounding the core region and comprising one or more main metals. In one embodiment, the total loading of the main metals in the catalyst is greater than or equal to 1 wt. %, e.g., from 1 to 25 wt. %. More than 85% of main metals are located in the surface region, based on the total loading of the main metals in the catalyst. Due to predominance of main metals in the surface region, in one embodiment, less than 15% of main metals are located in the core region, based on the total loading of the main metals in the catalyst. The main metals may comprise one or more of palladium, platinum, copper, iron, nickel, zinc, silver, chromium, tin, vanadium, or cobalt. In one exemplary embodiment, the main metals comprise platinum in an amount from 0.1 to 1.5 wt. %, tin in an amount from 0.1 wt. % to 10 wt. %, and cobalt in an amount from 0.6 wt. % to 10 wt. %.

The surface region has a maximum thickness that is less than 30% of the maximum thickness of the core region. In one embodiment, the surface region has a maximum thickness of less than 300 µm.

In one embodiment, the core region further comprises a Group IIA metal and at least one support material. The Group IIA metal may be selected from the group consisting of calcium, magnesium, and mixtures thereof. The support material may be selected from the group consisting of silica, silica/alumina, alumina, zirconia, and titania. In one embodiment, the support material has a surface area from 0.01 to 600 m²/g. The support material has a morphology selected from the group consisting of pellets, extrudates, spheres, spray dried microspheres, rings, pentarings, trilobes, quadrilobes, and multi-lobal shapes. It should be understood that the morphology of the support material is generally the morphology of the catalyst.

In one embodiment, the surface region may comprise two or more layers. There may be a first layer comprising cobalt, wherein more than 90% of the cobalt is located in the first layer, based on the total loading of the cobalt in the catalyst in the catalyst, and a second layer comprising one or more second layer metals, wherein more than 90% of second layer metals are located in the second layer, based on the total loading of the second layer metals in the catalyst. The second layer metals comprise one or more of palladium, platinum, copper, iron, nickel, zinc, silver, chromium, or tin. When two or more layers are used, the first layer surrounds the core region and the second layer contacts an outer edge of the solid catalyst. In addition, the first layer may at least partially overlap the second layer. The first layer may have a maximum thickness of less than 600 µm and the second layer may have a maximum thickness of less than 200 µm.

In a second embodiment, the invention is related to a process for producing ethanol, comprising contacting a feed stream comprising acetic acid, ethyl acetate, or mixtures thereof and hydrogen in a reactor in the presence of the solid catalyst, under conditions effective to form ethanol. The solid catalyst may comprise a core region, and a surface region surrounding the core region and comprising one or more main metals, wherein more than 85% of main metals are located in the surface region, based on the total loading of the main metals in the catalyst, as described herein. In one embodiment, the solid catalyst is capable of a selectivity to ethanol of at least 80% and an acetic acid conversion that is greater than 70%.

In a third embodiment, the invention is related to a core region, and a surface region comprising: a first layer comprising cobalt, wherein more than 90% of the cobalt are located in the first layer, based on the total loading of the cobalt in the catalyst, and a second layer comprising one or more second layer metals, wherein more than 90% of the second layer metals are located in the second layer, based on the total loading of the second layer metals in the catalyst; wherein the first layer surrounds the core region and the second layer contacts an outer edge of the solid catalyst, and wherein the total loading of cobalt and second layer metal is greater than 1 wt. %, e.g. from 1 to 25 wt. %. The core region further comprises a Group IIA metal being selected from the group consisting of calcium, magnesium, and mixtures thereof. In one embodiment, the second layer metal comprise one or more of palladium, platinum, copper, iron, nickel, zinc, silver, chromium, or tin. In addition, the first layer may at least partially overlap the second layer. In other embodiments, the first layer may be a discrete layer from the second layer. The first layer may have a maximum thickness of less than 600 µm and the second layer may have a maximum thickness of less than 200 µm. This catalyst may further be used in a process for producing ethanol by contacting a feed stream comprising acetic acid, ethyl acetate, or mixtures thereof and hydrogen in a reactor.

BRIEF DESCRIPTION OF DRAWINGS

The invention may be more completely understood in consideration of the following detailed description of various embodiments of the invention in connection with the accompanying drawings, wherein like numerals designate similar parts.

DETAILED DESCRIPTION OF THE INVENTION

The present invention relates to processes for producing ethanol by hydrogenating acetic acid, ethyl acetate, or mixtures thereof in the presence of a solid catalyst comprising a core region and a surface region that surrounds the core region. The main metals are distributed so that the majority of the main metals are in the surface region. This makes the catalysts of the present invention more active with a higher conversion of reactants and greater selectivity to ethanol.

During the hydrogenation of acetic acid to ethanol there are four principal reactions:

$$CH_3COOH + H_2 \rightarrow CH_3CHO + H_2O \qquad (I)$$

$$CH_3CHO + H_2 \rightarrow CH_3CH_2OH \qquad (II)$$

Without being bound by theory, it is believed that reactions III and IV are mass transfer limited, which may limit the conversion of acetic acid to ethanol. A solid catalyst of the present invention overcomes the mass transfer limitations, in particular of reactions III and IV, by increasing the metal concentrations near the surface of the catalyst. The concentration of metals that are active in the reactions, namely, main metals, are distributed to be near the surface of the catalyst. Surprisingly and unexpectedly, the solid catalysts of the present invention provide advantageous performance over catalysts having metals evenly dispersed throughout the catalyst.

Figure 1:
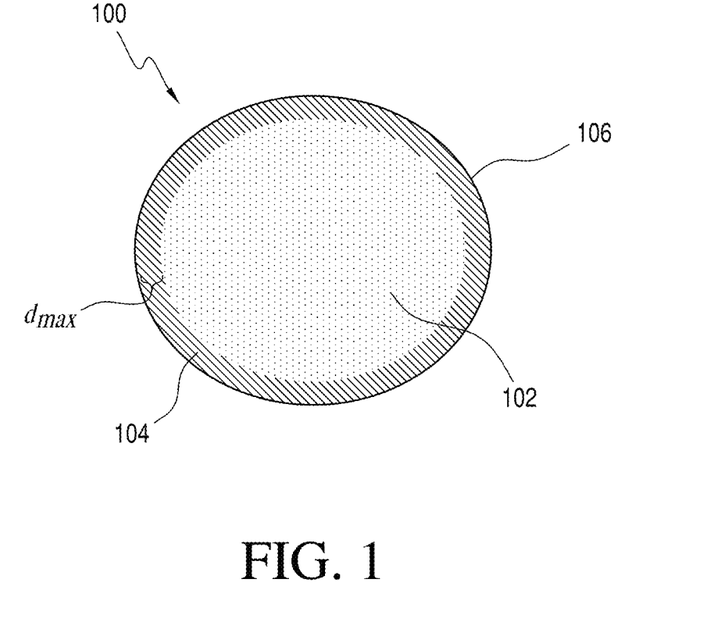
FIG. 1 is a cross-sectional view of a solid catalyst having a surface region surrounding the core region in accordance with one embodiment of the present invention.

In one embodiment, as shown in FIG. 1, the solid catalyst 100 comprises a core region 102 that is surrounded by a surface region 104. Surface region 104 abuts outer edge 106 of solid catalyst 100. For purposes of the present application, the term "surrounds" includes completely surrounding and partially surrounding such that less than 10% of the core region 102 is exposed to the outer edge 106, and more preferably less than 5%. When the phrase "at least partially surrounding" is used, it is understood to include completely surrounding.

The main metals for the catalytic activity are predominately dispersed in surface region 104 so that a greater percentage of main metals, in terms of mass and/or volume dispersion, are in surface region 104 as compared to core region 102. As discussed further herein, the main metals comprise one or more of palladium, platinum, copper, iron, nickel, zinc, silver, chromium, tin, vanadium, or cobalt. In one preferred embodiment, the main metals include platinum, tin, and cobalt. The total loading of the main metals in the catalyst may be greater than or equal to 1 wt. %, e.g., greater than or equal to 5 wt. %. In terms of ranges, the total loading of the main metals is from 1 wt. % to 25 wt. %, e.g., from 2.5 to 15 wt. %. In one embodiment, more than 85% of main metals, based on the total loading of the main metals in the catalyst, are located in the surface region, and more preferably more than 90%. In terms of ranges, from 85% to 99% of main metals are located in the surface region, based on the total loading of the main metals in the catalyst. For example, when the solid catalyst contains 5 wt. % main metals, the dispersion of the metals would be that the surface region contains at least 4.25 wt. % main metals, and the core region contains less than 0.75 wt. %.

The maximum thickness ($d_{max}$) of surface region 104, e.g., from core region 102 to outer edge 106, may be less than 30% of the maximum thickness of solid catalyst 100, and more preferably less than 10% or less than 5%. This allows a majority of the main metals to be dispersed in the outermost 1 to 30% of the volume of solid catalyst 100. This gives the solid catalyst an "egg shell" arrangement. For purposes of the present invention, thickness may be determined by a cross section of the solid catalyst. The actual thickness of surface region 104 may vary below the maximum thickness. The maximum thickness may also depend on the thickness of the core region, and morphology of the catalyst. In one embodiment, the maximum thickness of the surface region may be less than 300 μm, e.g., less than 180 μm. In terms of ranges the maximum thickness may vary from 20 to 300 μm, e.g., from 50 to 180 μm.

The core region may comprise a Group IIA metal selected from the group consisting of calcium, magnesium, and mixtures thereof. The core region also comprises a support material, as described herein. In one embodiment, more than 99% of the Group IIA metal based on the total loading of Group IIA metal in the catalyst is located in core region 102. Core region 102 also has less than 15% of main metals are located in the core region, based on the total loading of the main metals in the catalyst, and more preferably less than 10%. In terms of ranges, from 1% to 15% of main metals are located in the core region, based on the total loading of the main metals in the catalyst, and more preferably from 1% to 10%.

Figure 2A:
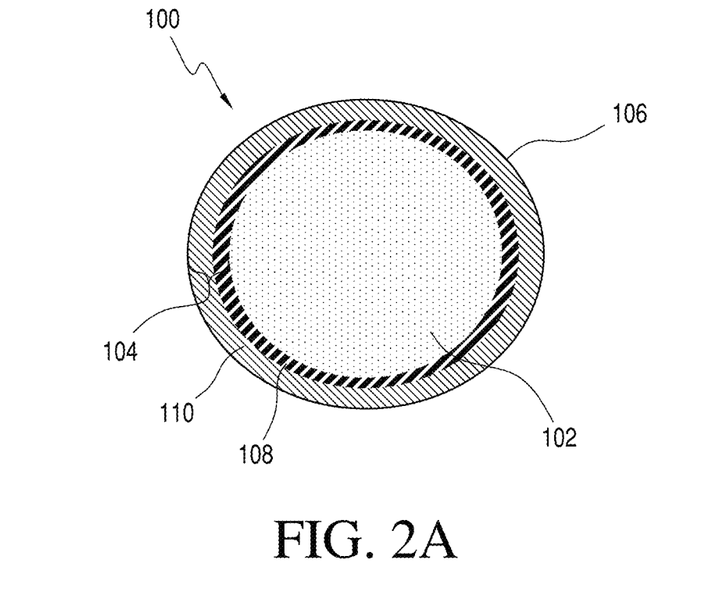
FIG. 2A is a cross-sectional view of a solid catalyst having a surface region that surrounds the core region in accordance with one embodiment of the present invention.
Figure 2B:
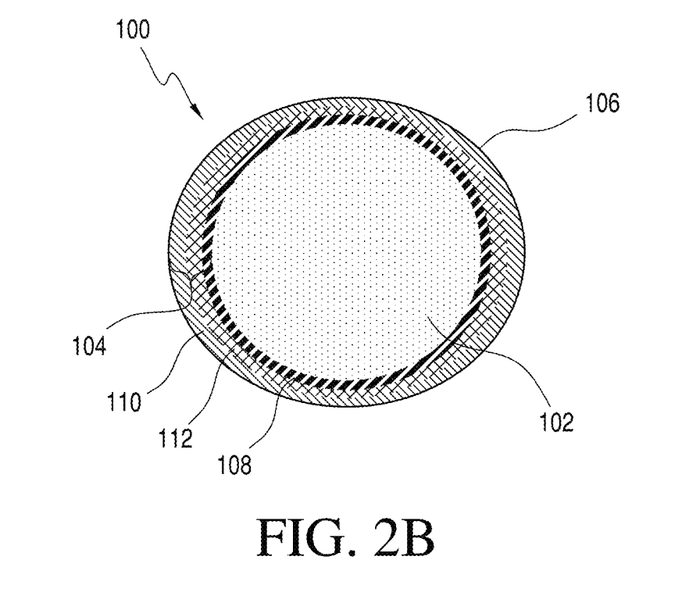
FIG. 2B is a cross-sectional view of a solid catalyst having a surface region with two layers and which surrounds the core region in accordance with one embodiment of the present invention.
Figure 3:
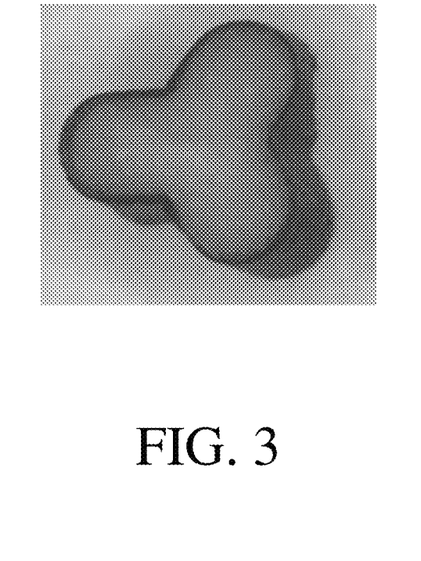
FIG. 3 is a light micrograph illustration of a cross-section of a solid catalyst having a trilobe morphology of the present invention.

In another embodiment, the surface region may comprise two or more layers. As shown in FIGS. 2A and 2B, surface region 104 may comprise two layers, a first layer 108 and a second layer 110. In one embodiment, first layer 108 comprises cobalt and second layer 110 comprises one or more second layer metals. More than 90% of the cobalt is located in the first layer, based on the total loading of the cobalt in the catalyst, e.g., more than 95%. Thus, the core region has less than 10% of the cobalt based on the total loading of the cobalt in the catalyst. The one or more second layer metals may comprise one or more of palladium, platinum, copper, iron, nickel, zinc, silver, chromium, or tin. In one preferred embodiment, the second layer metals include platinum and tin. Also, more than 90% of second layer metals are located in the second layer, based on the total loading of the second layer metals in the catalyst e.g., more than 95%. In one embodiment, the core region and first layer may have less than 10% of second layer metals based on the total loading of the second layer metals in the catalyst. More particularly, the core region may have less than 5% of second layer metals, based on the total loading of the second layer metals in the catalyst, e.g., less than 3%.

In one embodiment, the maximum thickness of first layer may be greater than the maximum thickness of the second layer. The maximum thickness of first layer may be less than 600 μm, e.g., less than 500 μm or less than 400 μm. In terms of ranges, the first layer may have a thickness from 50 μm to 600 μm, e.g., from 100 μm to 500 μm. The maximum thickness of second layer may be less than 200 μm, e.g., less than 180 μm or less than 150 μm. In terms of ranges, the first layer may have a thickness from 10 μm to 200 μm, e.g., from 30 μm to 180 μm.

As shown in FIG. 2A, first layer 108 abuts core region 102 and second layer 110 abuts outer edge 106 to form to discrete layers. In some embodiments, as shown in FIG. 2B, first layer 108 and second layer 110 may at least partially overlap to form an overlapping region 112. When an overlapping region 112 exists, first layer 108 and second layer 110 may abut outer edge 106. Thus, second layer 110 may be completely overlapping with first layer 108. Preferably, first layer 108 abuts core region 102 when there is an overlapping region 112, and the second layer 110 is not in contact with core region 102. When there is an overlapping region 112, more than 90% of the cobalt is located in the first layer and second layer, based on the total loading of the cobalt in the catalyst, e.g., more than 95%. More than 95% of second layer metals are located in the first layer and second layer, based on the total loading of the second layer metals in the catalyst, e.g., more than 97%.

Further discussion of the catalyst components is provided herein.

Main Metals

The catalyst of the invention comprises one or more main metals. The total weight of all main metals present in the solid catalyst preferably is from 1 to 25 wt. %, e.g., from 1.5 to 20 wt. %, or from 2.5 wt. % to 15 wt. %. For purposes of the present specification, unless otherwise indicated, weight percent is based on the total weight of the catalyst. The main metals in the catalyst may be present in different forms, for example in the form of one or more metal oxides. For purposes of determining the weight percent of the metals in the catalyst, the weight of any oxygen that is bound to the metal is ignored.

Since the solid catalysts of the present invention may include two or more metals, one metal may act as the active metal while another metal acts as a promoter metal. For instance, with a platinum/tin catalyst, platinum may be considered to be the active metal and tin may be considered the promoter metal. This should not be taken as an indication of the underlying mechanism of the catalytic activity. In some embodiments, the two or more main metals may be alloyed with one another or may comprise a non-alloyed metal solution or mixture.

As stated above, the main metals comprise one or more of palladium, platinum, copper, iron, nickel, zinc, silver, chromium, tin, vanadium, or cobalt. In one embodiment, the loading of the palladium and/or platinum may be low to reduce costs. In one embodiment, the palladium and/or platinum may be present in an amount from 0.05 to 5 wt. %, e.g. from 0.1 to 3 wt. %, from 0.1 to 1.5 wt. %, or from 0.3 to 0.7 wt. %. The loading of copper, iron, nickel, zinc, silver, chromium, and/or tin may be from 0.1 and 10 wt. %, e.g., from 0.5 to 8 wt. %, or from 1 to 5 wt. %. The loading of cobalt and/or vanadium may be from 0.6 to 10 wt. %, e.g., 0.6 to 7 wt. % cobalt, from 0.5 to 5 wt. % or from 1 to 4 wt. %. Thus, in one exemplary embodiment, the solid catalyst may have the following loadings: platinum in an amount from 0.1 to 1.5 wt. %; tin in an amount from 0.1 wt. % to 10 wt. %; and cobalt in an amount from 0.6 wt. % to 10 wt. %.

As indicated above, when the surface region has two layers, cobalt and/or vanadium may be present in a first layer than abuts the core region and the second layer may contain second layer metals comprising one or more of palladium, platinum, copper, iron, nickel, zinc, silver, chromium, or tin. The loadings of the second layer metals are the same as described above.

Preferably, the main metals of the present invention are substantially free of ruthenium, lanthanum, cerium, rhenium, tungsten, molybdenum, niobium, and tantalum. Substantially free means that the catalyst does not contain these metals beyond trace amounts of less than 0.0001 wt. %. Thus, the core region and surface region of the solid catalyst are substantially free of these metals.

Exemplary main metal bimetal combinations for the solid catalyst of the present invention may include the following: Pd/Cu, Pd/Fe, Pd/Ni, Pd/Zn, Pd/Ag, Pd/Cr, Pd/Sn, Pt/Cu, Pt/Fe, Pt/Ni, Pt/Zn, Pt/Ag, Pt/Cr, or Pt/Sn. Preferably the main metal bimetal combinations may include Pd/Sn or Pt/Sn. In another embodiment, the main metal trimetal combinations may include the following: Pd/Cu/Co, Pd/Fe/Co, Pd/Ni/Co, Pd/Zn/Co, Pd/Ag/Co, Pd/Cr/Co, Pd/Sn/Co, Pt/Cu/Co, Pt/Fe/Co, Pt/Ni/Co, Pt/Zn/Co, Pt/Ag/Co, Pt/Cr/Co, Pt/Sn/Co, Pt/Sn/Zr, Pt/Sn/Ni, Pd/Cu/Co, Pd/Fe/V, Pd/Ni/V, Pd/Zn/V, Pd/Ag/V, Pd/Cr/V, Pd/Sn/V, Pt/Cu/V, Pt/Fe/V, Pt/Ni/V, Pt/Zn/V, Pt/Ag/V, Pt/Cr/V, or Pt/Sn/V.

Core Region

As stated above, the core region comprises a Group IIA metal and a support material. In one embodiment, less than 15% of main metals are located in the core region, based on the total loading of the main metals in the catalyst, and more preferably less than 10%. More preferably, less than 10% of the cobalt is located in the core region, based on the total loading of the cobalt in the catalyst in the catalyst and less than 5% of second layer metals are located in the core region, based on the total loading of the second layer metals in the catalyst.

The Group IIA metal may be selected from the group consisting of calcium, magnesium, and mixture thereof. In one embodiment, the Group IIA metal may be present in an amount from 0.2 to 25 wt. %, e.g., from 0.5 to 20 wt. % or from 3 to 9 wt. %. For purposes of the present invention, more than 99% of the Group IIA metal is located in the core region, based on the total loading of Group IIA in the catalyst.

Depending on how the Group IIA metal is incorporated into the support material, the core region may have discrete concentrations of Group IIA metals or an even dispersion of the Group IIA metal in the core region.

In one embodiment, the Group IIA metal may be considered to be a support modifier. Without being bound by theory, the support modifiers may adjust the acidity of the support material. For example, the acid sites, e.g. Brønsted or Lewis acid sites, on the support material may be adjusted by the second support modifier to favor selectivity to ethanol during the hydrogenation of acetic acid. The acidity of the support material may be adjusted by reducing the number or reducing the availability of Brønsted or Lewis acid sites on the support material. The support material may also be adjusted by changing the pKa of the support material by using the second support modifier. Unless the context indicates otherwise, the acidity of a surface or the number of acid sites thereupon may be determined by the technique described in F. Delannay, Ed., "Characterization of Heterogeneous Catalysts"; Chapter III: Measurement of Acidity of Surfaces, p. 370-404; Marcel Dekker, Inc., N.Y. 1984, the entirety of which is incorporated herein by reference.

In addition to the metal precursors and preparation conditions employed, metal-support interactions may have a strong impact on selectivity to ethanol. In particular, the use of support modifiers that adjust the acidity can favor formation of ethanol over other hydrogenation products.

Accordingly, without being bound by theory, modification and stabilization of support materials for the catalysts of the present invention by incorporation of non-volatile support modifiers having either the effect of: counteracting acid sites present upon the support surface or the effect of thermally stabilizing the surface makes it possible to achieve desirable improvements in selectivity to ethanol, prolonged catalyst life, or both. In general, support modifiers based on oxides in their most stable valence state will have low vapor pressures and thus have low volatility or are rather non-volatile. Accordingly, it is preferred that the support modifiers are provided in amounts sufficient to: (i) counteract acidic sites present on the surface of the support material; (ii) impart resistance to shape change under hydrogenation temperatures; or (iii) both. Without being bound by theory, imparting resistance to shape change refers to imparting resistance, for example, to sintering, grain growth, grain boundary migration, migration of defects and dislocations, plastic deformation and/or other temperature induced changes in microstructure.

In preferred embodiments, the second modifier comprises a basic support modifier having a low volatility or that is non-volatile. Low volatility modifiers have a rate of loss that is low enough such that the acidity of the support modifier is not reversed during the life of the catalyst. Such basic modifiers, for example, may be selected from the group consisting of alkaline earth metal oxides or metasilicates of the alkaline earth metals. In one aspect, the support modifier is selected from the group consisting of oxides and metasilicates of any of magnesium, calcium, and mixtures thereof. The support modifier is substantially free of other compounds such as alkali metals, Group IIB metals and Group IIIB metals.

As the support modifier, e.g., calcium metasilicate, may tend to have a lower surface area than some support materials, such as silica. In one embodiment the support material comprises at least about 80 wt. %, e.g., at least about 85 wt. % or at least about 90 wt. %, high surface area silica in order to counteract this effect of including calcium metasilicate.

The core region also comprises a support material. As will be appreciated by those of ordinary skill in the art, support materials are selected such that the catalyst system is suitably active, selective and robust under the process conditions employed for the formation of ethanol. Suitable support materials may include, for example, stable metal oxide-based supports or ceramic-based supports. Preferred supports include supports such as silica, silica/alumina, alumina, zirconia, titania and mixtures thereof. Other supports may be used in some embodiments of the present invention, including without limitation, iron oxide, magnesium oxide, carbon, graphite, high surface area graphitized carbon, activated carbons, and mixtures thereof.

In one embodiment, the support material may be present in an amount from 50 wt. % to 99 wt. %, e.g., from 60 wt. % to 97 wt. % or from 70 wt. % to 95 wt. %. For purposes of determining the weight percent of the support material in the solid catalyst, the weight of entire support material, including any oxygen is included.

In the case where silica is used as the support material, it is beneficial to ensure that the amount of aluminum, which is a common contaminant for silica, is low, preferably less than 1 wt. %, e.g., less than 0.5 wt. % or less than 0.3 wt. %, based on the total weight of the support material. In this regard, pyrogenic silica is preferred as it commonly is available in purities exceeding 99.7 wt. %. High purity silica, as used throughout the application, refers to silica in which acidic contaminants such as aluminum are present, if at all, at levels of less than 0.3 wt. %, e.g., less than 0.2 wt. % or less than 0.1 wt. %. In cases where the support comprises a support modifier in the range from 2 wt. % to 10 wt. %, larger amounts of acidic impurities, such as aluminum, can be tolerated so long as they are substantially counter-balanced by an appropriate amount of a support modifier.

The solid catalysts of the present invention may allow for the use of very low surface area support materials. In general, the surface area of the support material may be from 0.01 to 600 m$^2$/g, e.g., from 0.1 to 300 m$^2$/g. Supports of alumina (having less than 1 wt. % SiO$_2$) or silica/alumina (having from 5 to 20 wt. % SiO$_2$) may have low surface area from 0.01 to 75 m$^2$/g, e.g, from 0.1 to 50 m$^2$/g. Silica supports (having more than 99 wt. % SiO$_2$), alumina, titania, and zirconia may have a surface area from 40 to 600 m$^2$/g, e.g., from 50 to 500 m$^2$/g or from 100 to 300 m$^2$/g. For purposes of the present specification, surface area refers to BET nitrogen surface area, meaning the surface area as determined by ASTM D6556-04, the entirety of which is incorporated herein by reference.

The support material also preferably has an average pore diameter from 1 to 200 nm, e.g., from 2 to 100 nm, from 4 to 25 nm, as determined by mercury intrusion porosimetry, and an average pore volume from 0.5 to 2.0 cm$^3$/g, e.g., from 0.7 to 1.5 cm$^3$/g, as determined by mercury intrusion porosimetry.

The morphology of the support material, and hence of the resulting catalyst composition, may vary widely. In some exemplary embodiments, the morphology of the support material and/or of the catalyst composition may be pellets, extrudates, spheres, spray dried microspheres, rings, pentarings, trilobes, quadrilobes, or multi-lobal shapes. Typically, the shapes are chosen empirically based upon perceived ability to contact the vapor phase with the catalytic agents effectively. In one aspect, the support material may have a shape having an increase surface area relative to the length, such as a trilobe or quadrilobe shape. Preferably, the support material has a morphology that allows for a packing density from 0.1 to 1.0 g/cm$^3$, e.g., from 0.2 to 0.9 g/cm$^3$ or from 0.3 to 0.8 g/cm$^3$. In terms of size, the support material preferably has an average particle size, e.g., meaning the diameter for spherical particles or equivalent spherical diameter for non-spherical particles, from 0.1 to 25 mm, e.g., from 1 to 15 mm or from 2 to 10 mm. The support material may have a length from 0.5 to 50 mm, e.g. from 1 to 10 mm or from 3 to 7 mm. The surface region of the solid catalyst is relatively small as compared to the core region and thus the thickness of the surface region should not significantly impact the morphology or size of the overall catalyst particles. Thus, the above particle sizes generally apply to both the size of the core region as well as to the solid catalyst of the present invention.

Without reference to the dispersion of the metals in the solid catalyst, the catalyst composition of the present invention may be represented by the formula:

$$F_wS_xCo_yM_zSiO_v,$$

wherein: F is one main metal selected from the group consisting of palladium, platinum, and combinations thereof; S is another main metal selected from the group consisting of copper, iron, nickel, zinc, silver, chromium, tin, and combinations thereof; M is a Group IIA metal selected from the group consisting of magnesium, calcium, and mixtures thereof; w is from 0.00001 to 0.008, e.g., from 0.00002 to 0.0001; x is from 0.00005 to 0.002, e.g., from 0.00005 to 0.0001; y is from 0.025 to 0.5, e.g., from 0.03 to 0.4; z is from 0.01 to 0.2, e.g., from 0.02 to 0.09; and v being selected to satisfy valence requirements. In one embodiment, y is selected to be greater than w+x, and/or z is selected to be greater than w+x. Depending on the Group IIA metal, y may be at least 2z or more.

In one exemplary embodiment, the catalyst composition of the present invention may be represented by the formula:

$$Pt_wSn_xCo_yCa_zSiO_v,$$

wherein: w is from 0.00001 to 0.008, e.g., from 0.00002 to 0.0001; x is from 0.00005 to 0.002, e.g., from 0.00005 to 0.0001; y is from 0.025 to 0.5, e.g., from 0.03 to 0.4; z is from 0.01 to 0.2, e.g., from 0.02 to 0.09; and v being selected to satisfy valence requirements. In one embodiment, y is selected to be greater than w+x, and/or z is selected to be greater than w+x. In addition, y may be at least 2z or more.

In another aspect, the support material may comprise alumina. In such aspects, the catalyst composition of the present invention may be represented by the formula:

$$F_wS_xCo_yM_zAl_aSiO_v,$$

wherein: F is one main metal selected from the group consisting of palladium, platinum, and combinations thereof; S is another main metal selected from the group consisting of copper, iron, nickel, zinc, silver, chromium, tin, and combinations thereof; M is a Group IIA metal selected from the group consisting of magnesium, calcium, and mixtures thereof; w is from 0.00001 to 0.008, e.g., from 0.00002 to 0.0001; x is from 0.00005 to 0.002, e.g., from 0.00005 to 0.0001; y is from 0.025 to 0.5, e.g., from 0.03 to 0.4; z is from 0.01 to 0.2, e.g., from 0.02 to 0.09; u is from 0.00001 to 0.01, e.g., from 0.00005 to 0.001; and v being selected to satisfy valence requirements. In aspect, z is greater than u.

One advantage of the solid catalysts of the present invention is the stability or activity of the catalyst for producing ethanol. Accordingly, it can be appreciated that the catalysts of the present invention are fully capable of being used in commercial scale industrial applications for hydrogenation of acetic acid, particularly in the production of ethanol. In particular, it is possible to achieve such a degree of stability such that catalyst activity will have rate of productivity decline that is less than 6% per 100 hours of catalyst usage, e.g., less than 3% per 100 hours or less than 1.5% per 100 hours. [We are using same numbers as previous applications] Preferably, the rate of productivity decline is determined once the catalyst has achieved steady-state conditions.

Preparation Process of the Solid Catalyst

The solid catalysts of the present invention may be prepared according to any known method that results in the dispersion of main metals between the core region and surface region. Specific drying or heating steps at atmospheric conditions or under vacuum that are well known by those skilled in the art may be employed in order to facilitate the distribution of the main metals, i.e., metals or the oxides thereof, either in the surface region.

For example, the solid catalysts may be prepared by sequential impregnation of the main metals onto a modified, pre-shaped support that may contain a Group IIA metal. First, a precursor of one of the main metals preferably is used in the metal impregnation step, such as a water-soluble compound or water-dispersible compound/complex. Impregnation occurs by adding; optionally drop wise, the main metal precursor, preferably in suspension or solution, to the dry support material comprising the Group IIA metal, referred to as a modified support. The resulting mixture may then be heated, e.g., optionally under vacuum, in order to remove the solvent. Additional drying and calcining may be then performed, optionally with ramped heating to form a modified support. Upon heating and/or the application of vacuum, the metal precursor preferably decomposes into the elemental or oxide form. In some cases, additional solvent or further impregnation steps may be used. During the heating (calcination) step, or at least during the initial phase of use of the catalyst, the elemental and/or oxide forms are converted into a catalytically active form of the metal or a catalytically active oxide thereof. Additional modification may be carried out by subsequent impregnation of additional metal(s) onto the modified support, either simultaneously (co-impregnation) or sequentially. The metal precursors are added to the modified support in soluble or water-dispersible form, and followed by drying and calcination.

Without being bound by theory, during preparation when cobalt or a precursor thereof is added to a support material having a Group IIA, the cobalt tends to evenly disperse. This gives the catalyst a purple shade of color. Upon calcination and addition of other main metals, the cobalt disperses along the surface of the catalyst, forming a blue ring around the core region.

Use of Solid Catalyst to Hydrogenate Carboxylic Acids

The process of hydrogenating a carboxylic acid, such as acetic acid, or ester thereof to form ethanol according to one embodiment of the invention may be conducted in a variety of configurations using a fixed bed reactor or a fluidized bed reactor as one of skill in the art will readily appreciate. In many embodiments of the present invention, an "adiabatic" reactor can be used; that is, there is little or no need for internal plumbing through the reaction zone to add or remove heat. Alternatively, a shell and tube reactor provided with a heat transfer medium can be used. In many cases, the reaction zone may be housed in a single vessel or in a series of vessels with heat exchangers therebetween. It is considered significant that acetic acid reduction processes using the catalysts of the present invention may be carried out in adiabatic reactors as this reactor configuration is typically far less capital intensive than tube and shell configurations.

Typically, the solid catalyst is employed in a fixed bed reactor, e.g., in the shape of an elongated pipe or tube where the reactants, typically in the vapor form, are passed over or through the catalyst. Other reactors, such as fluid or ebullient bed reactors, can be employed, if desired. In some instances, the hydrogenation catalysts may be used in conjunction with an inert material to regulate the pressure drop of the reactant stream through the catalyst bed and the contact time of the reactant compounds with the catalyst particles.

In one embodiment, the feed stream for the hydrogenation reaction may comprise acetic acid, ethyl acetate, or mixture thereof. In some embodiments, it is preferred to use pure acetic acid as a fresh feed and recycle small amounts of ethyl acetate. Thus, in one embodiment, the feed stream may comprise greater than 95 wt. % acetic acid and less than 5 wt. % ethyl acetate. In other embodiment, the feed stream may comprise a mixture having from 70 to 95 wt. % acetic acid, and from 5 to 30 wt. % ethyl acetate.

The hydrogenation reaction may be carried out in either the liquid phase or vapor phase. Preferably the reaction is carried out in the vapor phase under the following conditions. The reaction temperature may the range from of 125° C. to 350° C., e.g., from 200° C. to 325° C., from 225° C. to about 300° C., or from 250° C. to about 300° C. The pressure may range from 100 kPa to 3000 kPa (about 1 to 30 atmospheres), e.g., from 100 kPa to 2700 kPa, or from 100 kPa to 2300 kPa. The reactants may be fed to the reactor at a gas hourly space velocities (GHSV) of greater than 500 $hr^{-1}$, e.g., greater than 1000 $hr^{-1}$, greater than 2500 $hr^{-1}$ and even greater than 5000 $hr^{-1}$. In terms of ranges the GHSV may range from 50 $hr^{-1}$ to 50,000 $hr^{-1}$, e.g., from 500 $hr^{-1}$ to 30,000 $hr^{-1}$, from 1000 $hr^{-1}$ to 10,000 $hr^{-1}$, or from 1000 $hr^{-1}$ to 6500 $hr^{-1}$.

In another aspect of the process of this invention, the hydrogenation reaction is carried out at a pressure just sufficient to overcome the pressure drop across the catalytic bed at the GHSV selected, although there is no bar to the use of higher pressures, it being understood that considerable pressure drop through the reactor bed may be experienced at high space velocities, e.g., 5000 $hr^{-1}$ or 6500 $hr^{-1}$.

Although the reaction consumes two moles of hydrogen per mole of acetic acid to produce one mole of ethanol, the actual molar ratio of hydrogen to acetic acid in the feed stream may vary from about 100:1 to 1:100, e.g., from 50:1 to 1:50, from 20:1 to 1:2, or from 12:1 to 1:1. Most preferably, the molar ratio of hydrogen to acetic acid is greater than 4:1, e.g., greater than 5:1 or greater than 10:1.

Contact or residence time can also vary widely, depending upon such variables as amount of acetic acid, catalyst, reactor, temperature and pressure. Typical contact times range from a fraction of a second to more than several hours when a catalyst system other than a fixed bed is used, with preferred contact times, at least for vapor phase reactions, from 0.1 to 100 seconds, e.g., from 0.3 to 80 seconds or from 0.4 to 30 seconds.

The acetic acid may be vaporized at the reaction temperature, and then the vaporized acetic acid can be fed along with hydrogen in undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid.

In particular, using solid catalysts and processes of the present invention may achieve favorable conversion of acetic acid and favorable selectivity and productivity to ethanol. For purposes of the present invention, the term conversion refers to the amount of acetic acid in the feed that is convert to a compound other than acetic acid. Conversion is expressed as a mole percentage based on acetic acid in the feed.

The conversion of acetic acid (AcOH) is calculated from gas chromatography (GC) data using the following equation:

$$\text{AcOH Conv. (\%)} = 100 * \frac{\text{mmol AcOH (feed)} - \text{mmol AcOH (product)}}{\text{mmol AcOH (feed)}}$$

For purposes of the present invention, the conversion may be at least 40%, e.g., at least 60% or at least 80%. Although catalysts that have high conversions are desirable, such as at least 80% or at least 90%, a low conversion may be acceptable at high selectivity for ethanol.

"Selectivity" is expressed as a mole percent based on converted acetic acid. It should be understood that each compound converted from acetic acid has an independent selectivity and that selectivity is independent from conversion. For example, if 50 mole % of the converted acetic acid is converted to ethanol, we refer to the ethanol selectivity as 50%. Selectivity to ethanol (EtOH) is calculated from gas chromatography (GC) data using the following equation:

$$\text{EtOH Sel. (\%)} = 100 * \frac{\text{mmol EtOH (product)}}{\text{mmol AcOH (feed)} - \text{mmol AcOH (product)}}$$

For purposes of the present invention, the selectivity to ethanol of the catalyst is at least 80%, e.g., at least 85% or at least 88%. In embodiments of the present invention is also desirable to have low selectivity to undesirable products, such as methane, ethane, and carbon dioxide. The selectivity to these undesirable products is less than 4%, e.g., less than 2% or less than 1%. Preferably, no detectable amounts of these undesirable products are formed during hydrogenation. In several embodiments of the present invention, formation of alkanes is low, usually under 2%, often under 1%, and in many cases under 0.5% of the acetic acid passed over the catalyst is converted to alkanes, which have little value other than as fuel.

Productivity refers to the grams of a specified product, e.g., ethanol, formed during the hydrogenation based on the kilogram of catalyst used per hour. In one embodiment of the present invention, a productivity of at least 200 grams of ethanol per kilogram catalyst per hour, e.g., at least 400 grams of ethanol or least 600 grams of ethanol, is preferred. In terms of ranges, the productivity preferably is from 200 to 3,000 grams of ethanol per kilogram catalyst per hour, e.g., from 400 to 2,500 or from 600 to 2,000.

In another embodiment, the invention is to a crude ethanol product formed by processes of the present invention. The crude ethanol product produced by the hydrogenation process of the present invention, before any subsequent processing, such as purification and separation, typically will comprise primarily unreacted acetic acid and ethanol. In some exemplary embodiments, the crude ethanol product comprises ethanol in an amount from 15 wt. % to 70 wt. %, e.g., from 20 wt. % to 50 wt. %, or from 25 wt. % to 50 wt. %, based on the total weight of the crude ethanol product. Preferably, the crude ethanol product contains at least 22 wt. % ethanol, at least 28 wt. % ethanol or at least 44 wt. % ethanol. The crude ethanol product typically will further comprise unreacted acetic acid, depending on conversion, for example, in an amount from 0 to 80 wt %, e.g., from 5 to 80 wt %, from 20 to 70 wt. %, from 28 to 70 wt. % or from 44 to 65 wt. %. Since water is formed in the reaction process, water will also be present in the crude ethanol product, for example, in amounts ranging from 5 to 30 wt. %, e.g., from 10 to 30 wt. % or from 10 to 26 wt. %. Other components, such as, for example, esters, ethers, aldehydes, ketones, alkanes, and carbon dioxide, if detectable, collectively may be present in amounts less than 10 wt. %, e.g., less than 6 or less than 4 wt. %. In terms of ranges other components may be present in an amount from 0.1 to 10 wt. %, e.g., from 0.1 to 6 wt. %, or from 0.1 to 4 wt. %. Thus, exemplary crude ethanol compositional ranges in various embodiments of the invention are provided below in Table 1.

TABLE 1

CRUDE ETHANOL PRODUCT COMPOSITIONS

| Component | Conc. (wt. %) | Conc. (wt. %) | Conc. (wt. %) | Conc. (wt. %) |
|---|---|---|---|---|
| Ethanol | 15-70 | 15-70 | 20-50 | 25-50 |
| Acetic Acid | 5-80 | 20-70 | 28-70 | 44-65 |
| Water | 5-30 | 5-30 | 10-30 | 10-26 |
| Other | <10 | <10 | <6 | <4 |

The raw materials used in connection with the process of this invention may be derived from any suitable source including natural gas, oil, coal, biomass and so forth. It is well known to produce acetic acid through methanol carbonylation, acetaldehyde oxidation, ethylene oxidation, oxidative fermentation, and anaerobic fermentation. In one embodiment, the acetic acid is formed from methanol and carbon monoxide, wherein each of the methanol, the carbon monoxide, and hydrogen for the hydrogenating step is derived from syngas, and wherein the syngas is derived from a carbon source selected from the group consisting of natural gas, oil, coal, biomass, and combinations thereof. As petroleum and natural gas prices fluctuate becoming either more or less expensive, methods for producing acetic acid and intermediates such as methanol and carbon monoxide from alternate carbon sources have drawn increasing interest. In particular, when petroleum is relatively expensive compared to natural gas, it may become advantageous to produce acetic acid from synthesis gas ("syn gas") that is derived from any available carbon source. U.S. Pat. No. 6,232,352, the disclosure of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syn gas is diverted from the methanol synthesis loop and supplied to a separator unit to recover CO and hydrogen, which are then used to produce acetic acid. In addition to acetic acid, the process can also be used to make hydrogen which may be utilized in connection with this invention.

U.S. Pat. No. RE 35,377, also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form synthesis gas. The syn gas is converted to methanol which may be carbonylated to acetic acid. The method likewise produces hydrogen which may be used in connection with this invention as noted above. U.S. Pat. No. 5,821,111 discloses a process for converting waste biomass through gasification into synthesis gas as well as U.S. Pat. No. 6,685,754, the disclosures of which are incorporated herein by reference.

Alternatively, acetic acid in vapor form may be taken directly as crude product from the flash vessel of a methanol carbonylation unit of the class described in U.S. Pat. No. 6,657,078, the entirety of which is incorporated herein by reference. The crude vapor product, for example, may be fed directly to the ethanol synthesis reaction zones of the present invention without the need for condensing the acetic acid and light ends or removing water, saving overall processing costs.

Ethanol, obtained from hydrogenation processes of the present invention, may be used in its own right as a fuel or subsequently converted to ethylene which is an important commodity feedstock as it can be converted to polyethylene, vinyl acetate and/or ethyl acetate or any of a wide variety of other chemical products. In another application, the finished ethanol composition may be dehydrated to produce ethylene. Any known dehydration catalyst, such as zeolite catalysts or phosphotungstic acid catalysts, can be employed to dehydrate ethanol, as described in copending U.S. Pub. Nos. 2010/0030002 and 2010/0030001 and WO2010146332, the entire contents and disclosures of which are hereby incorporated by reference.

Ethanol may also be used as a fuel, in pharmaceutical products, cleansers, sanitizers, hydrogenation transport or consumption. Ethanol may also be used as a source material for making ethyl acetate, aldehydes, and higher alcohols, especially butanol. In addition, any ester, such as ethyl acetate, formed during the process of making ethanol according to the present invention may be further reacted with an acid catalyst to form additional ethanol as well as acetic acid, which may be recycled to the hydrogenation process.

The invention is described in detail below with reference to numerous embodiments for purposes of exemplification and illustration only. Modifications to particular embodiments within the spirit and scope of the present invention, set forth in the appended claims, will be readily apparent to those of skill in the art.

The following examples describe the procedures used for the preparation of various catalysts employed in the process of this invention.

EXAMPLES

Figure 4:
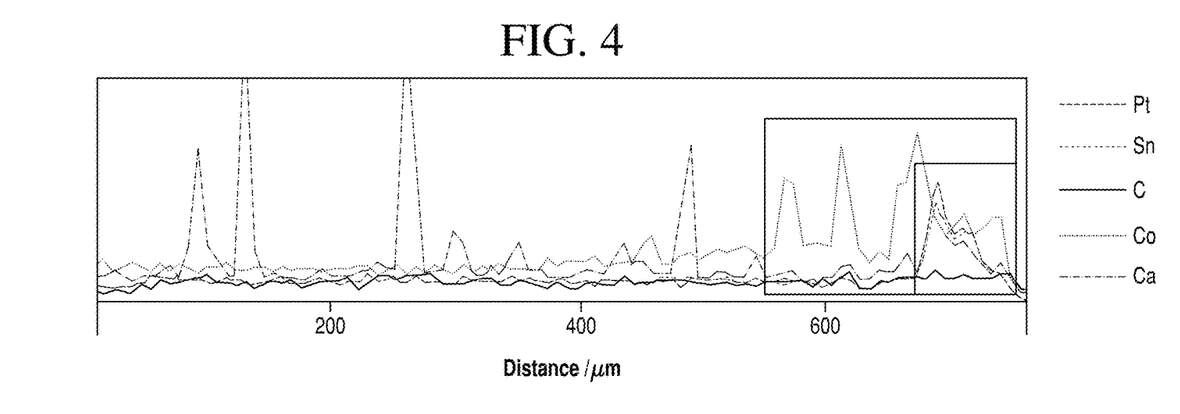
FIG. 4 is a graph of the metal dispersion in a solid catalyst of the present invention.
Figure 5:
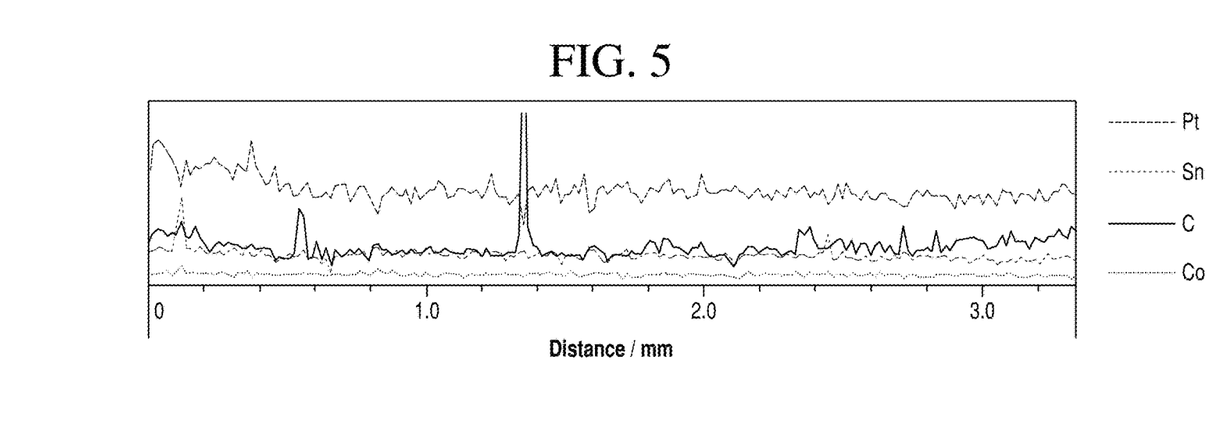
FIG. 5 is a graph of the metal dispersion in a catalyst having metals distributed throughout the catalyst.

Two catalysts were prepared with the same composition of $CaSiO_3$ 5.6 wt. %, $Co_3O_4$ 6.7 wt. %, Pt 0.5 wt. %, and Sn 0.6 wt. % on a silica support material. The solid catalysts were prepared to have a dispersion of main metals (i.e. greater than 85% of the total loading of main metals) as follows: 280 μm layer (maximum thickness) of cobalt and 155 μm layer (maximum thickness) of platinum and tin. This gave an egg-shape dispersion. The layer of cobalt overlapped the layer of platinum and tin. The distribution of metals is exemplified in FIG. 4. Comparative examples were also prepared to have an even distribution of metals as exemplified in FIG. 5.

The catalysts were tested for performance data for acetic acid hydrogenation to ethanol and ethyl acetate. The testing procedure involved 4 g of solid catalyst having a trilogy morphology and a length of 4.5 mm. The reaction temperature was 260° C. the pressure was 2169.75 kPa (300 psig). The flow rate of $H_2$ was 342 sccm and the flow rate AcOH was 0.092 g/min. Conversions, selectivities, and productivities were measured. The results from the catalyst testing are summarized in Table 2.

TABLE 2

| [SiO$_2$—CaSiO$_3$(5.6)—Co$_3$O$_4$(6.7)]—Pt(0.5)—Sn(0.6) | | | | | |
|---|---|---|---|---|---|
| | HOAc Conv. | Product Selectivity (wt %) | | | EtOH Prod. |
| Example | (%) | EtOH | EtOAc | AcH | Acetal | (g/kg/h) |
| 1 | 78 | 88 | 10 | 1 | 1 | 628 |
| 2 | 88 | 90 | 8 | 1 | 1 | 724 |
| 3 | 84 | 91 | 8 | 1 | 1 | 729 |
| Comp. A | 39 | 83 | 13 | 1 | 2 | 316 |
| Comp. B | 54 | 87 | 11 | 1 | 1 | 417 |

As can be seen from the table, the combination of conversion of acetic acid and selectivity to ethanol was at its highest for the solid catalyst having a dispersion of metals near the surface of the catalyst in accordance with the present invention. That is, the Examples prepared in accordance with the present invention were found to have superior performance over the comparative examples having the same main metal loading.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A process for producing ethanol, comprising contacting a feed stream comprising acetic acid, ethyl acetate, or mixtures thereof and hydrogen in a reactor in the presence of a solid catalyst, under conditions effective to form ethanol, wherein the solid catalyst comprises
   a core region; and
   a surface region surrounding the core region and comprising one or more main metals; wherein the total loading of the main metals in the catalyst is greater than or equal to 1 wt. % and wherein more than 85% of main metals are located in the surface region, and less than 15% of main metals are located in the core region, based on the total loading of the main metals in the catalyst.

2. The process of claim 1, wherein 85% to 99% of main metals are located in the surface region.

3. The process of claim 1, wherein 1% to 15% of main metals are located in the core region.

4. The process of claim 1, wherein the solid catalyst is capable of a selectivity to ethanol of at least 80% and an acetic acid conversion that is greater than 70%.

5. The process of claim 1, wherein the core region further comprises a Group IIA metal.

6. The process of claim 5, wherein the Group IIA metal is selected from the group consisting of calcium, magnesium, and mixtures thereof.

7. The process of claim 1, wherein the main metals comprise one or more of palladium, platinum, copper, iron, nickel, zinc, silver, chromium, tin, vanadium, or cobalt.

8. The process of claim 1, wherein the main metals comprise platinum in an amount from 0.1 to 1.5 wt. %, tin in an amount from 0.1 wt. % to 10 wt. %, and cobalt in an amount from 0.6 wt. % to 10 wt. %.

9. The process of claim 1, wherein the total loading of the main metals is from 1 wt. % to 25 wt. %.

10. The process of claim 1, wherein the surface region has a maximum thickness of less than 300 µm.

11. The process of claim 1, wherein the surface region has a maximum thickness that is less than 30% of the maximum thickness of the core region.

12. The process of claim 1, wherein the core region comprises at least one support material selected from the group consisting of silica, silica/alumina, alumina, zirconia, and titania.

13. The process of claim 1, wherein the at least one support material has a surface area from 0.01 to 600 m$^2$/g.

14. The process of claim 1, wherein the support material has a morphology selected from the group consisting of pellets, extrudates, spheres, spray dried microspheres, rings, pentarings, trilobes, quadrilobes, and multi-lobal shapes.

15. The process of claim 1, wherein the surface region comprises
 a first layer comprising cobalt, wherein more than 90% of the cobalt is located in the first layer, based on the total loading of the cobalt in the catalyst in the catalyst; and
 a second layer comprising one or more second layer metals, wherein more than 90% of second layer metals are located in the second layer, based on the total loading of the second layer metals in the catalyst, wherein the second layer metals comprise one or more of palladium, platinum, copper, iron, nickel, zinc, silver, chromium, or tin,
 wherein the first layer surrounds the core region and the second layer contacts an outer edge of the solid catalyst.

16. The process of claim 15, wherein the core region further comprises a Group IIA metal being selected from the group consisting of calcium, magnesium, and mixtures thereof.

17. A process for producing ethanol, comprising contacting a feed stream comprising acetic acid, ethyl acetate, or mixtures thereof and hydrogen in a reactor in the presence of a solid catalyst, under conditions effective to form ethanol, wherein the solid catalyst comprises:
 a core region; and
 a surface region comprising:
  a first layer comprising cobalt, wherein more than 90% of the cobalt are located in the first layer, based on the total loading of the cobalt in the catalyst; and
  a second layer comprising one or more second layer metals, wherein more than 90% of the second layer metals are located in the second layer, based on the total loading of the second layer metals in the catalyst;
  wherein the first layer surrounds the core region and the second layer contacts an outer edge of the solid catalyst, wherein the total loading of cobalt and second layer metal is greater than 1 wt. %, and wherein the first layer has a maximum thickness of less than 600 µm and wherein the second layer has a maximum thickness of less than 200 µm.

18. The process of claim 17, wherein the first and second layer at least partially overlap.

19. The process of claim 17, wherein the second layer metal comprise one or more of palladium, platinum, copper, iron, nickel, zinc, silver, chromium, or tin.

* * * * *